(12) United States Patent
Sakai (10) Patent No.: US 8,629,412 B2
(45) Date of Patent: Jan. 14, 2014

(54) FLUORESCENCE INTENSITY CORRECTION METHOD, FLUORESCENCE INTENSITY CALCULATION METHOD, AND FLUORESCENCE INTENSITY CALCULATION DEVICE AND FLUORESCENCE INTENSITY CORRECTION PROGRAM

(75) Inventor: Yoshitsugu Sakai, Kanagawa (JP)

(73) Assignee: Sony Corporation, Tokyo (JP)

(*) Notice: Subject to any disclaimer, the term of this patent is extended or adjusted under 35 U.S.C. 154(b) by 75 days.

(21) Appl. No.: 13/196,102

(22) Filed: Aug. 2, 2011

(65) Prior Publication Data

US 2012/0049086 A1 Mar. 1, 2012

(30) Foreign Application Priority Data

Aug. 24, 2010 (JP) .................................. 2010-186949

(51) Int. Cl.
*G01J 1/58* (2006.01)
(52) U.S. Cl.
USPC ................... 250/459.1; 250/458.1; 250/462.1
(58) Field of Classification Search
USPC ....................................................... 250/458.1
See application file for complete search history.

(56) References Cited

U.S. PATENT DOCUMENTS 5,847,162 A * 12/1998 Lee et al. ...................... 549/227
2009/0012721 A1* 1/2009 Kimura et al. ................... 702/23

FOREIGN PATENT DOCUMENTS

JP 2003-83894 3/2003

* cited by examiner

*Primary Examiner* — David Porta
*Assistant Examiner* — Jeremy S Valentiner
(74) *Attorney, Agent, or Firm* — K&L Gates LLP

(57) ABSTRACT

A fluorescence intensity correction method including: receiving fluorescence emitted from fluorescent pigments, collecting detected values from each light detector, and obtaining a fluorescence spectrum of each fluorescent pigment as one spectrum group; separating the obtained spectrum group into a plurality of small spectrum groups; comparing the separated small spectrum groups with a fluorescence wavelength distribution of each fluorescent pigment obtained in advance and specifying the small spectrum groups as the fluorescence spectrum of any fluorescent pigment; comparing a differential spectrum between small spectrum groups that are not specified and one or more specified small spectrum groups with the fluorescence wavelength distribution of unspecified fluorescent pigments obtained in advance, and specifying the differential spectrum as the fluorescence spectrum of any fluorescent pigment; and calculating the intensity of fluorescence emitted from each fluorescent pigment.

7 Claims, 8 Drawing Sheets

$$\begin{Bmatrix} FL1 \\ FL2 \\ FL3 \\ FL4 \\ FL5 \end{Bmatrix} = \begin{Bmatrix} a_{11} & a_{21} & a_{31} & a_{41} & a_{51} \\ a_{12} & a_{22} & a_{32} & a_{42} & a_{52} \\ a_{13} & a_{23} & a_{33} & a_{43} & a_{53} \\ a_{14} & a_{24} & a_{34} & a_{44} & a_{54} \\ a_{15} & a_{25} & a_{35} & a_{45} & a_{55} \end{Bmatrix}^{-1} \begin{Bmatrix} PMT1 \\ PMT2 \\ PMT3 \\ PMT4 \\ PMT5 \end{Bmatrix}$$

FL1 TO FL5: TRUE FLUORESCENCE OF EACH FLUORESCENT PIGMENT
$a_{n1}$ TO $a_{n5}$: PROPORTION OF WAVELENGTH DISTRIBUTION OF FLUORESCENT PIGMENT n
PMT1 TO PMT5: EACH MEASURED FLUORESCENCE INTENSITY

FLUORESCENCE INTENSITY CORRECTION METHOD, FLUORESCENCE INTENSITY CALCULATION METHOD, AND FLUORESCENCE INTENSITY CALCULATION DEVICE AND FLUORESCENCE INTENSITY CORRECTION PROGRAM

CROSS REFERENCES TO RELATED APPLICATIONS

The present application claims priority to Japanese Priority Patent Application JP 2010-186949 filed in the Japan Patent Office on Aug. 24, 2010, the entire contents of which are hereby incorporated by reference.

BACKGROUND

The present application relates to a fluorescence intensity correction method or a fluorescence intensity calculation method, a fluorescence intensity calculation device, and a fluorescence intensity correction program. In more detail, the application relates to a fluorescence intensity correction method for accurately calculating the intensity of fluorescence that is emitted from each of a plurality of fluorescent pigments that are multiply labeled on microparticles, and the like.

In the past, devices (for example, flow cytometers) for measuring the properties of microparticles by labeling microparticles such as cells using fluorescent pigments and measuring the intensity and the pattern of the fluorescence emitted from the fluorescent pigments that are excited by being irradiated by laser light have been used. In recent years, in order to analyze the properties of cells and the like in more detail, multicolor measurement of labeling microparticles using a plurality of fluorescent pigments and measuring the light emitted from each fluorescent pigment by a plurality of light detectors (such as PMTs) having different light-receiving wavelength bands has been performed. In multicolor measurement, detection of fluorescence is performed by selecting an optical filter of the light detector side according to the fluorescence wavelength of the fluorescent pigment that is used.

On the other hand, the fluorescent pigments that are in current usage (for example, FITC, PE (PhycoErythrin), and the like) have wavelength bands that overlap one another in the fluorescence spectrum. Therefore, in a case when multicolor measurement is performed combining such fluorescent pigments, even if the fluorescence emitted from each fluorescent pigment is separated by wavelength bands by an optical filter, fluorescence from fluorescent pigments that are not the target may leak into each light detector. If leaking in of fluorescence occurs, a discrepancy occurs between the fluorescence intensity measured by each light detector and the true fluorescence intensity from the target fluorescent pigments, causing measurement error.

In order to correct for such measurement error, fluorescence correction of deducting the leaked-in fluorescence intensity from the fluorescence intensity measured by the light detectors is performed. Fluorescence correction adds electrical or mathematical correction to pulses in order that the fluorescence intensity measured at the light detectors becomes the true fluorescence intensity from the target fluorescent pigments.

Figure 9:
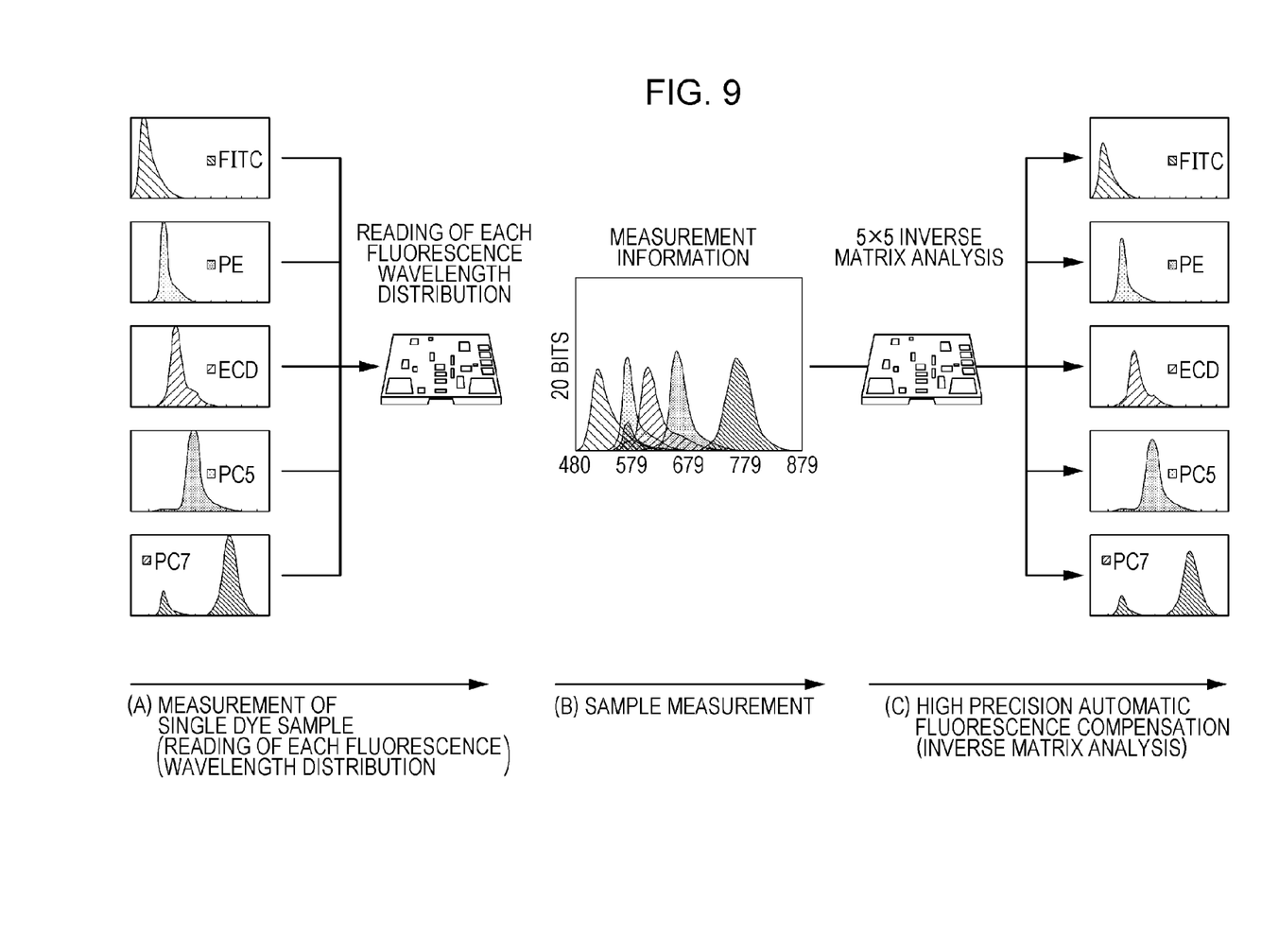
FIG. 9 is a diagram describing a fluorescence correction method using a correction matrix of the related art.
Figure 10:
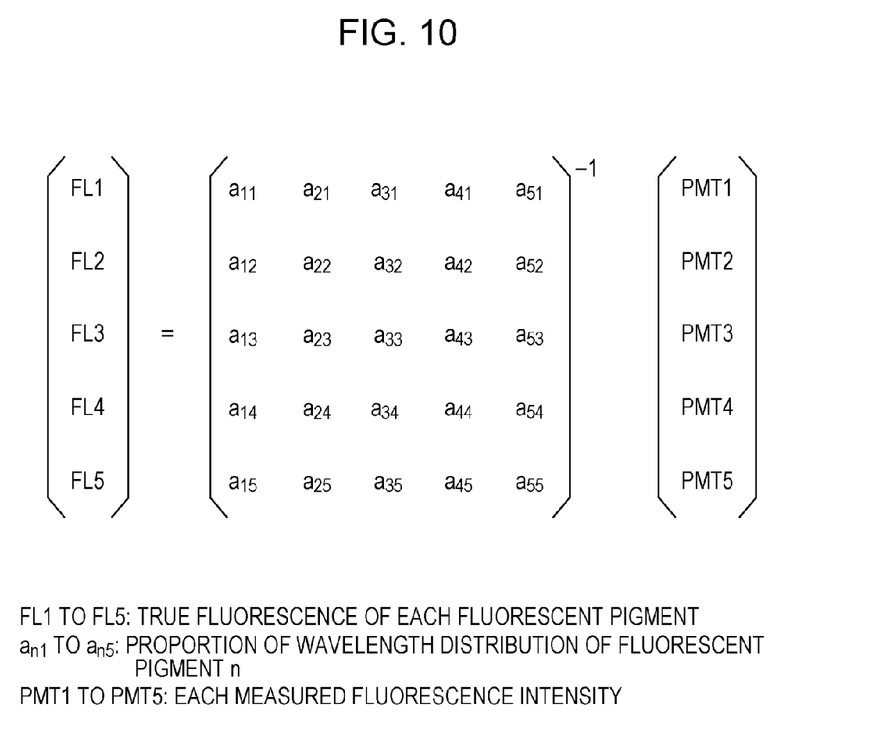
FIG. 10 is a diagram describing the matrix elements of the correction matrix of the related art.

As a method of performing fluorescence correction mathematically, a method of calculating the true fluorescence intensity from the target fluorescent pigments by representing the fluorescence intensity measured at each light detector as a vector and applying an inverse matrix of a leak-in matrix set in advance to the vector is used (refer to FIGS. 9 and 10 and Japanese Unexamined Patent Application Publication No. 2003-83894). The leak-in matrix is created by analyzing the fluorescence wavelength distribution of microparticles in which each florescent pigment is individually singly labeled, and in which the fluorescence wavelength distribution of each fluorescent pigment is arranged as a column vector. The inverse matrix of the leak-in matrix is also referred to as a "correction matrix". In FIGS. 9 and 10, as an example, a case when 5-color measurement using 5 kinds (FITC, PE, ECD, PC5, PC7) of fluorescent pigments and 5 light detectors is performed is illustrated.

SUMMARY

In the fluorescence correction method using the correction matrix, it is necessary for the fluorescence wavelength distribution of each fluorescent pigment to be recognized. For this reason, in the past, the fluorescence wavelength distribution of each fluorescent pigment has been obtained by analyzing the microparticles that are singly labeled for every sample analysis, or storing of a reference fluorescence wavelength distribution in the device in advance has been performed.

However, in a case when the reference fluorescence distribution that is stored in the device in advance is used, the effect of measurement error that occurs for every analysis of a sample is not able to be removed, and in order to perform an accurate measurement of the fluorescence intensity, correction by manual operation may often be necessary. Further, in a case when the fluorescence wavelength distribution obtained by analyzing the singly labeled microparticles is used, the more colors there are, the greater the time and effort involved in preparation before sample measurement.

In recent years, demand by users to increase the number of fluorescent pigments that are able to be used for analyzing the properties of cells and the like in more detail has been growing. Accordingly, according to an advantage of the application, it is desirable to provide a fluorescence correction method that is able to perform fluorescence correction using the fluorescence wavelength distribution of each fluorescent pigment without having to analyze the singly labeled microparticles for every sample analysis, and that is able to simply and accurately calculate the fluorescence intensity from each fluorescent pigment.

According to an embodiment, there is provided a fluorescence intensity correction method or a fluorescence intensity calculating method that includes the following:

receiving, by a plurality of light detectors having different light-receiving wavelength bands, the fluorescence emitted from fluorescent pigments that are excited by irradiating light on microparticles that are multiply labeled by a plurality of fluorescent pigments, collecting the detected values from each light detector, and obtaining the fluorescence spectrum of each fluorescent pigment as one spectrum group;

separating the obtained spectrum group into a plurality of small spectrum groups;

comparing the separated small spectrum groups with the fluorescence wavelength distribution of each fluorescent pigment obtained in advance and specifying the small spectrum groups as the fluorescence spectrum of any fluorescent pigment. Here, the spectrum group may be separated into a plurality of small spectrum groups by independent component analysis, principal component analysis, or the like;

comparing the differential spectrum between small spectrum groups that are not specified as the fluorescence spectrum of any fluorescent pigment and one or more specified small spectrum groups with the fluorescence wavelength distribution of unspecified fluorescent pigments obtained in advance, and specifying the differential spectrum as the fluorescence spectrum of any fluorescent pigment; and calculating the fluorescence intensity of the fluorescence emitted from each fluorescent pigment using the fluorescence wavelength distribution of the small spectrum group or the spectrum differential with regard to fluorescent pigments in which the small spectrum group or the differential spectrum is specified and using the fluorescence wavelength distribution obtained in advance with regard to fluorescent pigments in which the small spectrum group or the differential spectrum is not specified.

With the fluorescence intensity correction method and the like, the fluorescence wavelength distribution of each fluorescent pigment is able to be extracted from the spectrum group obtained by the measurement of microparticles, on which fluorescent pigments are multiply labeled, and used for the calculation of the fluorescence intensity. Further, in a case where there are fluorescent pigments of which the fluorescence wavelength distribution could not be extracted, only for such fluorescent pigments, the fluorescence intensity is calculated using the fluorescence wavelength distribution obtained in advance.

Specifically, for example, the intensity of fluorescence emitted from each fluorescent pigment may be calculated by arranging the fluorescence wavelength distribution of the small spectrum group or the spectrum differential as a column vector with regard to fluorescent pigments in which the small spectrum group or the differential spectrum is specified and using the inverse matrix of the leak-in matrix that is the fluorescence wavelength distribution obtained in advance arranged as a column vector with regard to fluorescent pigments in which the small spectrum group or the differential spectrum is not specified.

In addition, another embodiment provides a fluorescence intensity calculation device that includes the following sections.

A measuring section that receives, by a plurality of light detectors having different light-receiving wavelength bands, fluorescence emitted from fluorescent pigments that are excited by irradiating light on microparticles that are multiply labeled by a plurality of fluorescent pigments, collects the detected values from each light detector, and obtains the fluorescence spectrum of each fluorescent pigment as one spectrum group;

A calculating section that calculates the intensity of fluorescence emitted from each fluorescent pigment by separating the obtained spectrum group into a plurality of small spectrum groups, comparing the separated small spectrum groups with a stored fluorescence wavelength distribution of each fluorescent pigment and specifies the small spectrum groups as the fluorescence spectrum of any fluorescent pigment, comparing a differential spectrum between small spectrum groups that are not specified as the fluorescence spectrum of any fluorescent pigment and one or more specified small spectrum groups with the stored fluorescence wavelength distribution of unspecified fluorescent pigments, and specifies the differential spectrum as the fluorescence spectrum of any fluorescent pigment, and using the fluorescence wavelength distribution of the small spectrum group or the spectrum differential with regard to fluorescent pigments in which the small spectrum group or the differential spectrum is specified and by using the stored fluorescence wavelength distribution with regard to fluorescent pigments in which the small spectrum group or the differential spectrum is not specified.

The fluorescence intensity calculation device may further include an inputting section that receives input of information relating to fluorescent pigments used in fluorescent labeling of microparticles, and a storing section that stores the fluorescence wavelength distribution of each fluorescent pigment obtained in advance.

In addition, still another embodiment provides a fluorescence intensity correction program that executes the following:

receiving, by a plurality of light detectors having different light-receiving wavelength bands, fluorescence emitted from fluorescent pigments that are excited by irradiating light on microparticles that are multiply labeled by a plurality of fluorescent pigments, collecting detected values from each light detector, obtaining a fluorescence spectrum of each fluorescent pigment as one spectrum group, and separating the spectrum group into a plurality of small spectrum groups;

comparing the separated small spectrum groups with the stored fluorescence wavelength distribution of each fluorescent pigment and specifying the small spectrum groups as the fluorescence spectrum of any fluorescent pigment;

comparing a differential spectrum between small spectrum groups that are not specified as the fluorescence spectrum of any fluorescent pigment and one or more specified small spectrum groups with the stored fluorescence wavelength distribution of unspecified fluorescent pigments, and specifying the differential spectrum as the fluorescence spectrum of any fluorescent pigment; and calculating the intensity of fluorescence emitted from each fluorescent pigment using the fluorescence wavelength distribution of the small spectrum group or the spectrum differential with regard to fluorescent pigments in which the small spectrum group or the differential spectrum is specified and using the stored fluorescence wavelength distribution with regard to fluorescent pigments in which the small spectrum group or the differential spectrum is not specified.

In the application, "microparticles" widely includes biological microparticles such as cells, microorganisms, and liposomes, and synthetic particles such as latex particles, gel particles, and industrial particles, and the like.

Biological microparticles include chromosomes, liposomes, mitochondria, organelles, and the like that configure various types of cells. Cells include animal cells (hematopoietic cells and the like) and plant cells. Microorganisms include bacteria such as *Escherichia coli*, viruses such as the tobacco mosaic virus, and fungi such as yeast. Further, biological microparticles may also include biological high polymers such as nucleic acid, proteins, and complexes thereof. Furthermore, industrial particles may be, for example, organic or inorganic high polymer materials, metals, or the like. Organic high polymer materials include polystyrene, styrene-divinylbenzene, poly(methyl methacrylate), and the like. Inorganic high polymer materials include glass, silica, and magnetic materials. Metals include colloidal gold, aluminum, and the like. Although, in general, it is normal for the shapes of the microparticles to be spherical, they may be nonspherical, and the size and the mass thereof are not particularly limited.

According to the embodiments, a fluorescence correction method in which fluorescence correction is able to be performed using the fluorescence wavelength distribution of each fluorescent pigment without having to analyze the singly labeled microparticles for every sample analysis and the fluorescence intensity from each fluorescent pigment is able to be simply and accurately calculated is provided.

Additional features and advantages are described herein, and will be apparent from the following Detailed Description and the figures.

DETAILED DESCRIPTION

Embodiments of the present application will be described below in detail with reference to the drawings.

Further, the embodiments described below are representative examples of the embodiments, and the scope is not to be interpreted as limited thereby. Here, description will be given in the following order.

Figure 1:
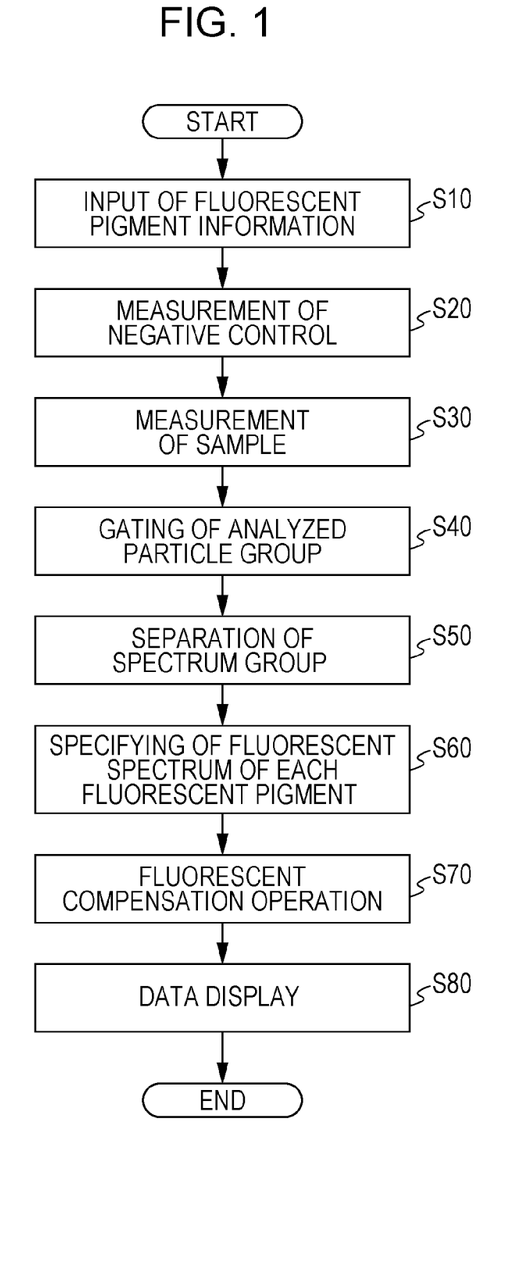
FIG. 1 is a flowchart describing the procedures of the fluorescence correction method according to an embodiment.
Figure 2:
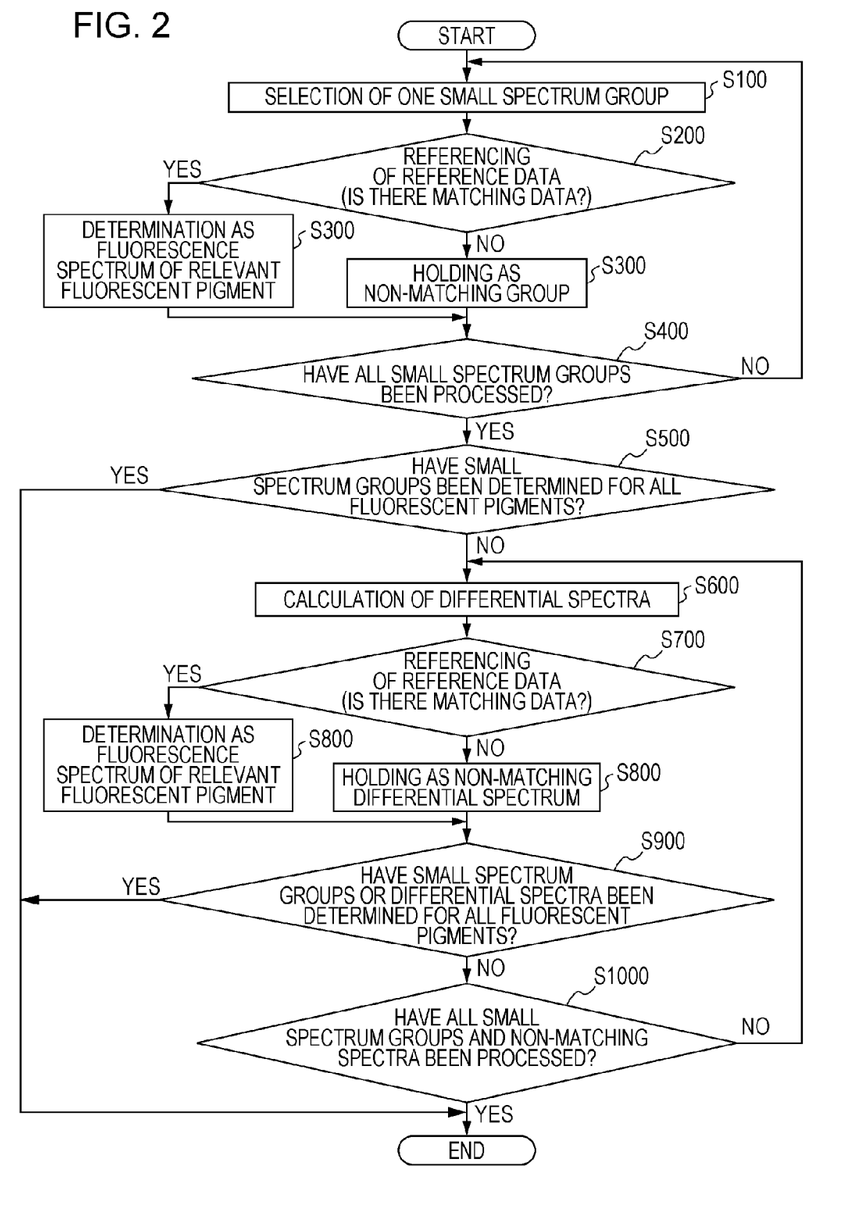
FIG. 2 is a flowchart describing the procedure of Step S60 in detail.

1. Fluorescence Intensity Correction Method
 1 Step S10: Input of Fluorescent Pigment Information
 2 Step S20: Measurement of Negative Control
 3 Step S30: Measurement of Sample
 4 Step S40: Gating of Analyzed Microparticle Group
 5 Step S50: Separation into Small Spectrum Groups
 6 Step S60: Specifying of Fluorescence Spectrum of Each Fluorescent Pigment
  6-1 Step S100: Selection of Small Spectrum Groups
  6-2 Step S200: Referencing of Reference Data
  6-3 Step S600: Calculation of Differential Spectra
  6-4 Step S700: Referencing of Reference Data
 7 Step S70: Fluorescence Correction Operation
 8 Step S80: Data Display
2. Specific Example of Processing of Step S50 (Separation into Small Spectrum Groups) and Step S60 (Specifying of Fluorescence Spectrum of Each Fluorescent Pigment)
 1 Step S50: Separation into Small Spectrum Groups
 2 Step S60: Specifying of Fluorescence Spectrum of Each Fluorescent Pigment
3. Fluorescence Intensity Calculation Device and Fluorescence Intensity Calculation Program
 1. Fluorescence Intensity Correction Method FIGS. 1 and 2 are flowcharts describing the procedures of the fluorescence correction method according to an embodiment. FIG. 2 is a flowchart describing the procedure of Step S60 in FIG. 1 in detail. The fluorescence intensity correction method according to an embodiment includes the following procedures.

"Step S30": procedure of receiving, by a plurality of light detectors having different light-receiving wavelength bands, the fluorescence emitted from fluorescent pigments that are excited by irradiating light on microparticles that are multiply labeled by a plurality of fluorescent pigments, collecting the detected values from each light detector, and obtaining the fluorescence spectrum of each fluorescent pigment as one spectrum group.

"Step S50": procedure of separating the obtained spectrum group into a plurality of small spectrum groups.

"Step S60 (S200)": procedure of comparing the separated small spectrum groups with the fluorescence wavelength distribution (reference data) of each fluorescent pigment obtained in advance and specifying the small spectrum groups as the fluorescence spectrum of any fluorescent pigment.

"Step S60 (S600 and S700)": procedure of comparing the differential spectrum between small spectrum groups that are not specified as the fluorescence spectrum of any fluorescent pigment and one or more specified small spectrum groups with the reference data of unspecified fluorescent pigments, and specifying the differential spectrum as the fluorescence spectrum of any fluorescent pigment.

"Step S70": procedure of calculating the fluorescence intensity of the fluorescence emitted from each fluorescent pigment using the fluorescence wavelength distribution of the small spectrum group or the spectrum differential with regard to fluorescent pigments in which the small spectrum group or the differential spectrum is specified and using the reference data with regard to fluorescent pigments in which the small spectrum group or the differential spectrum is not specified.

Figure 8:
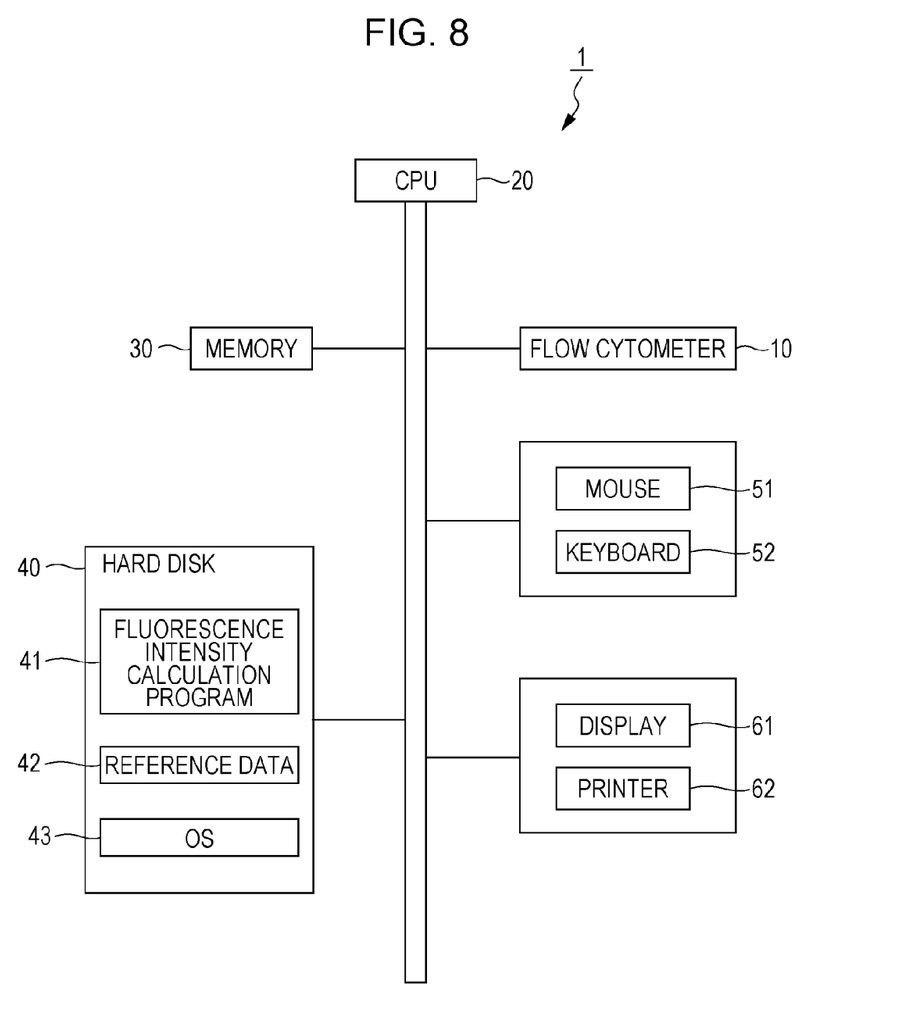
FIG. 8 is a block diagram illustrating the functional configuration of a fluorescence intensity calculation device according to an embodiment.

A fluorescence intensity calculation device 1 that is described later in detail with reference to FIG. 8 is, for example, used in the fluorescence intensity correction method according to an embodiment. The fluorescence intensity calculation device 1 includes a flow cytometer and a CPU, a memory, a hard disk, a user interface, and the like.

1 Step S10: Input of Fluorescent Pigment Information

First, the microparticles that are the measurement targets are multiply labeled using a plurality of fluorescent pigments. Fluorescent pigment labeling of the microparticles is able to be performed by a method recognized in the related art. For example, in a case when the measurement target is a cell, fluorescent label antibodies facing cell surface molecules and the cell are mixed, and the antibodies are bonded to the cell surface molecules. The fluorescent label antibodies may be antibodies with fluorescent pigments bonded directly thereto, and may have fluorescent pigments to which avidin is bonded to biotin-labeled antibodies bonded thereto by an avidin biotin reaction. Further, the antibodies may be monoclonal antibodies or polyclonal antibodies.

Two or more substances recognized in the related art are able to be combined and used as the fluorescent pigments. Phycoerythrin (PE), FITC, PE-Cy5, PE-Cy7, PE-Texas Red, allophycocyanin (APC), APC-Cy7, ethidium bromide, propidium iodide, Hoechst 33258/33342, DAPI, acridine orange, chromomycin, mithramycin, olivomycin, pyronin Y, thiazole orange, Rhodamine 101 isothiocyanate, BCECF, BCECF-AM, C.SNARF-1, C.SNARF-1-AMA, aequorin, Indo-1, Indo-1-AM, Fluo-3, Fluo-3-AM, Fura-2, Fura-2-AM, oxonol, Texas Red, Rhodamine 123, 10-N-nonyl-acrydine orange, fluorescein, fluorescein diacetate, carboxyfluorescein, carboxyfluorescein diacetate, carboxy dichlorofluorescein, and carboxy dichlorofluorescein diacetate can be given as examples.

In Step S10 of FIG. 1, information relating to the fluorescent pigments used in the fluorescent labeling of the microparticles (hereinafter, referred to as "fluorescent pigment information") is input to the fluorescence intensity calculation device 1 by the user. The fluorescent pigment information is input using a user interface such as a mouse or a keyboard. The fluorescence wavelength distribution (hereinafter, also referred to as "reference data") that is a reference relating to each fluorescent pigment is stored in the fluorescence intensity calculation device 1. Data that is stored in the device or data that is obtained by measuring the fluorescence wavelength distribution of each fluorescent pigment in advance is used as the reference data. Obtaining of the reference data is not performed for every sample analysis, and once the reference data is obtained and stored in the device, it is necessary to perform obtaining of the reference data for every sample analysis. The fluorescent pigment information that is input in the step is, for example, the name, the index number, or the like of a fluorescent pigment, and denotes information made to correspond with the reference data of each fluorescent pigment that is stored.

2 Step S20: Measurement of Negative Control

In Step S20 of FIG. 1, measurement of microparticles that are not labeled by fluorescent pigments (negative control) is performed by the user. The measurement of microparticles is able to be performed by the same method using a multicolor measurement flow cytometer recognized in the related art. In the present step, the fluorescence spectrum of the autofluorescence of the microparticles (background value) is obtained, and at the same time, the specificity of the fluorescent pigment labeling of the sample is ascertained.

3 Step S30: Measurement of Sample

In Step S30 of FIG. 1, measurement of microparticles (sample) that are labeled by fluorescent pigments is performed by the user. In the present step, by irradiating light on microparticles that are multiply labeled by a plurality of fluorescent pigments, the fluorescence emitted from the excited fluorescent pigments is received by a plurality of light detectors having different light-receiving wavelength bands. Further, detection values are collected from each light detector and the fluorescence spectrum of each fluorescent pigment is obtained as one spectrum group.

4 Step S40: Gating of Analyzed Microparticle Group

Step S40 of FIG. 1 is a procedure performed by the user as necessary, where a microparticle group on which analysis is to be performed is extracted from the sample (gating). The present step is performed, for example, in a case when only lymphocytes are analyzed out of a blood cell sample, or in a case when only living cells are analyzed out of a sample. In a case when the sample is composed only of microparticle groups that are to be analyzed, the present step is not necessary. By performing the step, the fluorescence spectrum group corresponding to the analyzed microparticle group is able to be appropriately extracted from the detected values of each light detector.

Gating is able to be performed similarly to the method by the flow cytometer recognized in the related art. Specifically, using a user interface such as a display, a mouse, or a keyboard, the microparticle group that is to be analyzed is designated on a two-dimensional correlation diagram in which forward scattered light (Forward Scatter: FSC) is the x-axis and side scattered light (Side Scatter: SSC) is the y-axis. Here, the present step may be a procedure that is automatically performed by a program.

5 Step S50: Separation into Small Spectrum Groups

In Step S50 of FIG. 1, a plurality of principal component groups (hereinafter, referred to as "small spectrum groups") is separated from the spectrum group obtained in Step S30 by the user or a program. The separation into small spectrum groups is performed, using a user interface such as a display, a mouse, or a keyboard in a case when it is performed by the user, by designating the component group on the spectrogram of the spectrum group. Further, in a case when the small spectrum groups are separated by a program, a commonly used component analysis algorithm such as independent component analysis or principal component analysis is applied.

The spectrum group obtained in Step S30 is submitted to the separation into small spectrum groups after subtracting the background value obtained in Step S20 from the data value thereof (fluorescence intensity).

6 Step S60: Specifying of Fluorescence Spectrum of Each Fluorescent Pigment

In Step S60 of FIG. 1, the fluorescence spectrum of each fluorescent pigment is specified by a program using the small spectrum group separated in Step S50 and the fluorescence wavelength distribution (reference data) of each fluorescent pigment obtained in advance. The procedure of the present step will be described in detail with reference to FIG. 2.

6-1 Step S100: Selection of Small Spectrum Groups

In the present step, first, one out of the plurality of small spectrum groups separated in Step S50 is selected. The selected small spectrum group is, out of the plurality of small spectrum groups separated in Step S50, preferably the one that is most clearly separated from the other small spectrum groups.

6-2 Step S200: Referencing of Reference Data

In the present step, the small spectrum group selected in Step S100 is compared with reference data, and reference data in which the fluorescence wavelength distribution pattern matches the small spectrum group is retrieved.

In a case when matching reference data is present, based on fluorescent pigment information corresponding to the reference data, the selected small spectrum group is determined as the fluorescence spectrum of the relevant fluorescent pigment and is stored. Further, in a case when matching reference data is not present, the selected small spectrum group is stored as a non-matching group (Step S300).

In Step S400 that follows, it is ascertained whether the entire processing of the plurality of small spectrum groups separated in Step S50 is complete. In a case when a small spectrum group of which processing is not complete is present, the processing is continued by returning to Step S100 with regard to that small spectrum group, and the step is repeated until the processing of all of the small spectrum groups is complete.

6-3 Step S600: Calculation of Differential Spectra

In Step S500, with regard to all of the fluorescent pigments in which the fluorescent pigment information is input in Step S10, it is ascertained whether or not the small spectrum groups in which the reference data and the fluorescence wavelength distribution pattern match are determined. That is, with regard to all of the fluorescent pigments used in the fluorescent labeling of the microparticles, it is ascertained whether or not the small spectrum groups that are considered the fluorescence spectra thereof are determined (refer to Step S500).

Here, in a case when small spectrum groups are determined with regard to all of the fluorescent pigments, the processing is ended. On the other hand, in a case when fluorescent pigments in which a small spectrum group is not determined are present, the following processing is performed in Step S600. That is, first, the differential spectrum between small spectrum groups that are not specified as the fluorescence spectrum of any fluorescent pigment and that are stored as non-matching groups in Step S300 and one or more specified small spectrum groups is calculated (Step S600). A plurality of differential spectra is calculated from one of the small spectrum groups stored as non-matching groups by combining one or two or more of the specified small spectrum groups and taking the differential.

There is a strong possibility that in the small spectrum groups that are not specified as the fluorescent spectrum of any fluorescent pigment and that are stored as non-matching groups in the procedures up to Step S400, the spectrum information of a plurality of fluorescent pigments is subjected to a convolution operation. In the present step, the effect of the convolution operation is cancelled by subtracting the data values of small spectrum groups that are already specified as the fluorescence spectrum of any fluorescent pigment from the data values of non-matching small spectrum groups.

6-4 Step S700: Referencing of Reference Data

In Step S700, the differential spectrum calculated in Step S600 is compared with the reference data, and the reference data in which the fluorescence wavelength distribution pattern matches the differential spectrum is retrieved.

In a case when matching reference data is present, based on the fluorescent pigment information corresponding to the reference data, the calculated differential spectrum is determined as the fluorescence spectrum of the relevant fluorescent pigment and is stored. Further, in a case when matching reference data is not present, the calculated differential spectrum is stored as a non-matching group (Step S800).

In Step S900 that follows, with regard to all of the fluorescent pigments to which the fluorescent pigment information is input in Step S10, it is ascertained whether a small spectrum group in which the fluorescence wavelength distribution pattern matches the reference data or the differential spectrum is determined. That is, with regard to all of the fluorescent pigments used in the fluorescent labeling of the microparticles, it is ascertained whether or not the small spectrum groups that are considered the fluorescence spectra thereof or the differential spectra are determined.

Here, in a case when the small spectrum group or the differential spectrum is determined for all of the fluorescent pigments, the processing is ended.

In Step S900, in a case when fluorescent pigments in which the small spectrum group or the differential spectrum is not determined are present, it is further ascertained whether the entire processing of the small spectrum groups that are stored as non-matching groups in Step S300 is complete (Step S1000). In a case when small spectrum groups in which processing is not complete are present, processing is continued by returning to Step S600 with regard to such small spectrum groups, and the step is repeated until the processing of all of the small spectrum groups is complete.

In Step S1000, in a case when it is confirmed that all of the small spectrum groups have been processed, the processing is ended. At this stage, a case in which fluorescent pigments in which the small spectrum group or the differential spectrum is not determined are present is also possible. There is a strong possibility that the fluorescent pigments in which the small spectrum group or the differential spectrum could not be determined were not specifically labeled on the microparticles.

7 Step S70: Fluorescence Correction Operation

In Step S70 of FIG. 1, the intensity of the fluorescence emitted from each fluorescent pigment is calculated using the fluorescence spectrum of each fluorescent pigment specified by a program in Step S60.

At this time, with regard to the fluorescent pigments in which the small spectrum group or the differential spectrum is specified in Step S60, the fluorescence intensity is calculated using the fluorescence wavelength distribution of the small spectrum group or the differential spectrum. Further, in Step S60, with regard to the fluorescent pigments in which the small spectrum group or the differential spectrum is not specified, the fluorescence intensity is calculated using the reference data.

Specifically, the detected value from each light detector is corrected by, for example, arranging the fluorescence wavelength distribution of the small spectrum group or the differential spectrum as a column vector with regard to the fluorescent pigments in which the small spectrum group or the differential spectrum is specified, and using the inverse matrix of the leak-in matrix that is the reference data arranged as a column vector with regard to the fluorescent pigments in which the small spectrum group or the differential spectrum is not specified. Here, the calculation of the fluorescence intensity is not limited to the method using the inverse matrix of the leak-in matrix.

8 Step S80: Data Display

In Step S80 of FIG. 1, the calculation result of the fluorescence intensity is displayed on a user interface such as a display by a program. The present step is able to be performed by a similar method by a flow cytometer recognized in the related art. Specifically, display by a two-dimensional correlation diagram, in which the fluorescence intensities of two different kinds of fluorescent pigments with regard to each microparticle are each plotted on the x-axis or the y-axis, is able to be adopted.

In the past, in a fluorescence correction method using a correction matrix, the fluorescence wavelength distribution of each fluorescent pigment has been obtained by analyzing the microparticles that are singly labeled for every sample analysis, or the reference data is stored in a device in advance. However, in the method of using the reference data of the related art, it is not possible to eliminate the effect of the measurement error that is caused for each sample analysis. Further, in a case when the fluorescence wavelength distribution obtained by analyzing the singly labeled microparticles is used, the more colors there are, the more time and effort is involved in the preparation before sample measurement.

With the fluorescence intensity correction method according to an embodiment, the correction matrix is able to be created by extracting the fluorescence wavelength distribution of each fluorescent pigment from the spectrum group obtained by the measurement of a sample in which fluorescent pigments are multiply labeled. Further, the correction matrix elements are configured using the reference data only with regard to the fluorescent pigments in which the fluorescent wavelength distribution could not be extracted. According to the fluorescence intensity correction method, therefore, without analyzing the singly-labeled microparticles for every sample analysis and by minimizing the effect of the measurement error caused for every sample analysis, the fluorescence intensity from each fluorescent pigment is able to be simply and accurately calculated.

2. Specific Example of Processing of Step S50 (Separation into Small Spectrum Groups) and Step S60 (Specifying of Fluorescence Spectrum of Each Fluorescent Pigment)

The specific processing details of Steps S50 and S60 of the fluorescence intensity correction method according to an embodiment will be described with reference to FIGS. 3 to 7. The spectrum group obtained by measuring the microparticles (refer to Step S30) that are multiply labeled by the four kinds of fluorescent pigments of FITC, PE, PE-TR, and PE-Cy5 using a 32-channel multicolor measurement flow cytometer is exemplified in FIG. 3A. The spectrograms of the small spectrum groups that are separated from the spectrum group are exemplified in FIGS. 3B to 3G. The spectrograms of the fluorescence wavelength distribution (reference data) obtained in advance by the analysis of the singly labeled microparticles with regard to FITC, PE, PE-TR, and PE-Cy5 are respectively exemplified in FIGS. 4 to 7. Since the reference data is data that includes the properties of a notch filter provided to prevent leak-in from an excitation laser (640 nm), the reference data becomes characteristic of the apparatus without perfectly matching the spectrum information of the pigment itself.

Figure 3A:
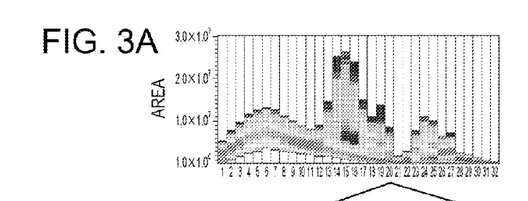
FIG. 3A is a spectrogram of a spectrum group obtained by measuring microparticles that are multiply labeled by four kinds of fluorescent pigments of FITC, PE, PE-TR, and PE-Cy5.

The microparticles are composed of a plurality of populations that show different dyeing affinities to the four kinds of fluorescent pigments of FITC, PE, PE-TR, and PE-Cy5, and the spectrum group of FIG. 3A obtained by measuring the microparticles has a mixture of the data of each population.

1 Step S50: Separation into Small Spectrum Groups

With the separation of small spectrum groups from the spectrum group of FIG. 3A, separation based on the characteristics of the dyeing affinity of each population is possible. For example, first, separation is possible by the level (or the presence or absence) of the detected value of channel 25. When separated by the detected value of channel 25, the spectrum group of FIG. 3A is separated into the small spectrum groups of FIGS. 3B and 3C. Next, if the small spectrum group of FIG. 3C is separated by the level of the detected value of channel 16, separation into the small spectrum groups of FIGS. 3D and 3E is possible. Further, if the small spectrum group of FIG. 3E is separated by the level of the detected value of channel 16, separation into the small spectrum groups of FIGS. 3F and 3G is possible.

By the above processing, four small spectrum groups of FIGS. 3B, 3D, 3F, and 3G are separated from the spectrum group of FIG. 3A.

2 Step S60: Specifying of Fluorescence Spectrum of Each Fluorescent Pigment

Figure 3B:
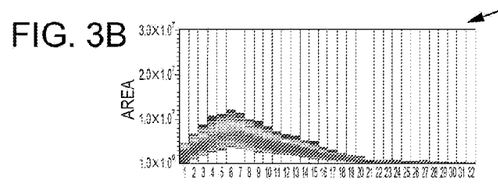
FIGS. 3B to 3G are spectrograms of small spectrum groups that are separated from the spectrum group.
Figure 3C:
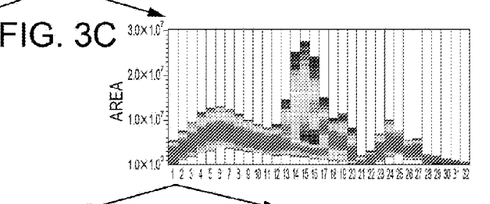
Figure 3D:
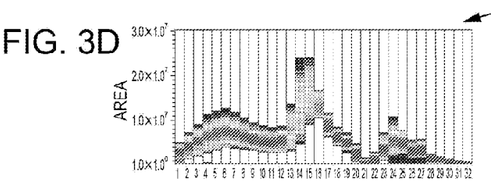
Figure 3E:
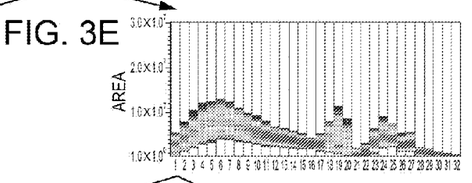
Figure 3F:
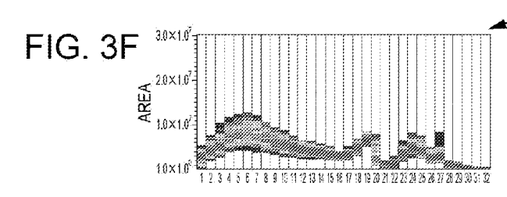
Figure 3G:
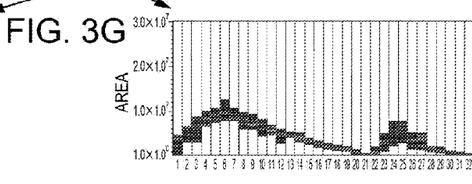
Figure 4:
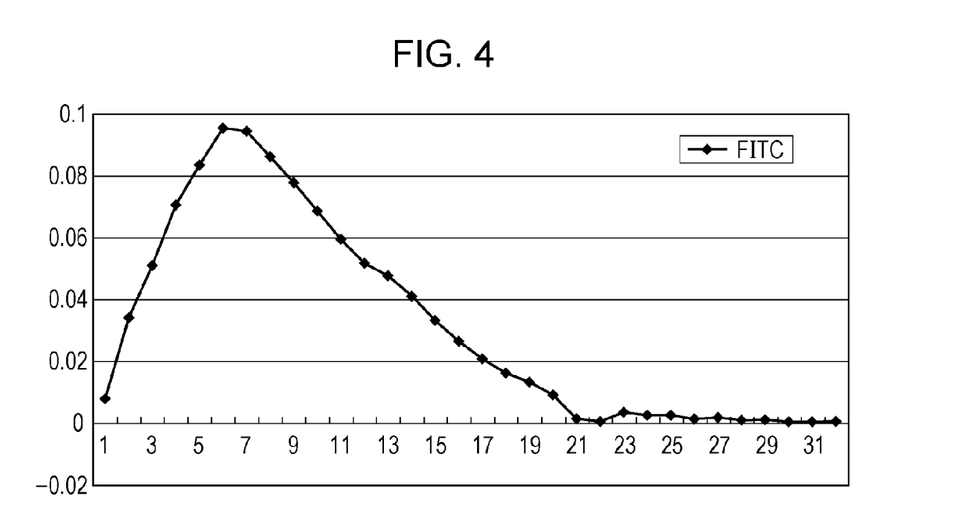
FIG. 4 is a spectrogram of reference data of FITC.
Figure 5:
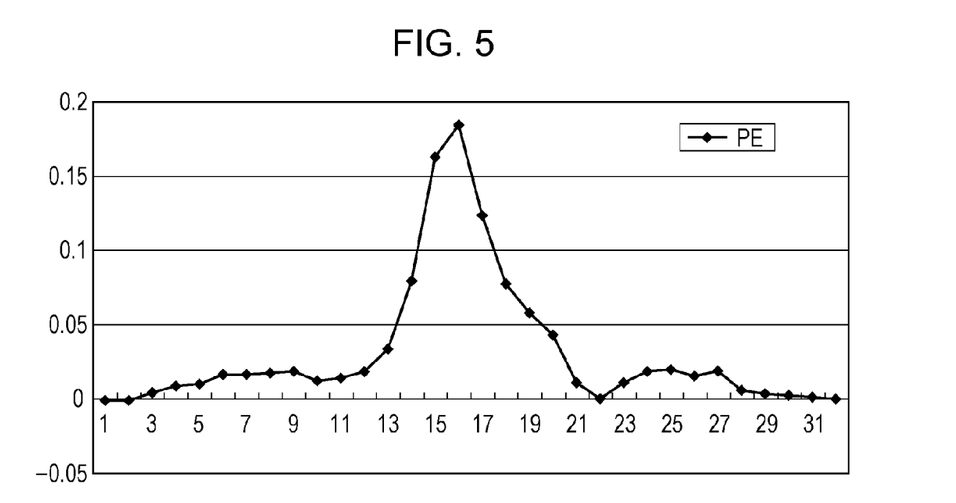
FIG. 5 is a spectrogram of reference data of PE.
Figure 6:
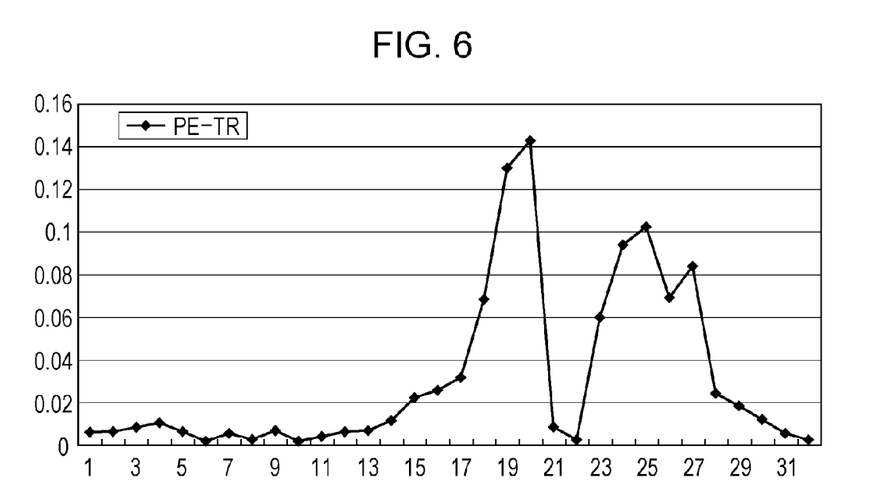
FIG. 6 is a spectrogram of reference data of PE-TR.
Figure 7:
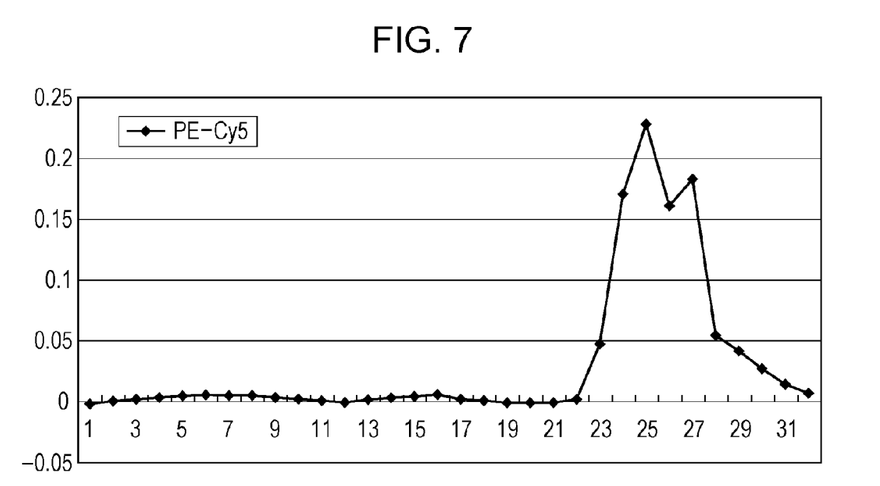
FIG. 7 is a spectrogram of reference data of PE-Cy5.

The small spectrum group of FIG. 3B is selected in Step S100. When the reference data is referenced in Step S200, the small spectrum group of FIG. 3B matches the fluorescence wavelength distribution pattern of FITC (refer to FIG. 4). Therefore, in Step S300, the small spectrum group of FIG. 3B is determined to be the fluorescence spectrum of FITC and stored. Since the small spectrum groups of FIGS. 3D, 3F, and 3G have not been processed in Step S400, Step S100 is returned to.

The small spectrum group of FIG. 3D is selected in Step S100. When the reference data is referenced in Step S200, there is no data that matches the fluorescence wavelength distribution pattern. Therefore, in Step S300, the small spectrum group of FIG. 3D is saved as a non-matching group. Since the small spectrum groups of FIGS. 3F and 3G have not been processed in Step S400, Step S100 is returned to.

The small spectrum group of FIG. 3F is selected in Step S100. When the reference data is referenced in Step S200, there is no data that matches the fluorescence wavelength distribution pattern. Therefore, in Step S300, the small spectrum group of FIG. 3F is saved as a non-matching group. Since the small spectrum group of FIG. 3G has not been processed in Step S400, Step S100 is returned to.

The small spectrum group of FIG. 3G is selected in Step S100. When the reference data is referenced in Step S200, there is no data that matches the fluorescence wavelength distribution pattern. Therefore, in Step S300, the small spectrum group of FIG. 3G is saved as a non-matching group. Since all of the small spectrum groups have been processed in Step S400, Step S500 is proceeded to.

In Step S500, since only the small spectrum group of FIG. 3B of FITC has been confirmed so far, Step S600 is proceeded to.

In Step 600, the differential spectrum between the small spectrum groups of FIGS. 3D, 3F, and 3G that are not specified as the fluorescence spectrum of any fluorescent pigment in Step S300 and saved as non-matching groups and the small spectrum group of FIG. 3B that is specified as the fluorescence spectrum of FITC is calculated.

Here, first, the differential spectrum (H) between the small spectrum group of FIG. 3D and the small spectrum group of FIG. 3B are taken. If the reference data is referenced, the spectrum difference (H) matches the fluorescence wavelength distribution pattern of PE (refer to FIG. 5). Therefore, in Step S800, the differential spectrum (H) is determined as the fluorescence spectrum of PE and is stored. Since the differential spectra of PE-TR and PE-Cy5 are not determined in Step S900, the step proceeds to Step S1000. Further, since the small spectrum groups of FIGS. 3F and 3G have not been processed in Step S1000, Step S600 is returned to.

In Step S600, the differential spectrum between the small spectrum group of FIG. 3F, the small spectrum group of FIG. 3B specified as the fluorescence spectrum of FITC, and/or the differential spectrum (H) specified as the fluorescence spectrum of PE is calculated. The differential spectrum (I) that is obtained by deducting the small spectrum group of FIG. 3B from the small spectrum group of FIG. 3F matches the fluorescence wavelength distribution pattern of PE-TR if the reference data is referenced (refer to FIG. 6). Therefore, in Step S800, the differential spectrum (I) is determined as the fluorescence spectrum of PE-TR and is stored. Since the differential spectrum of PE-Cy5 is not determined in Step S900, the step proceeds to Step S1000. Further, since the small spectrum group of FIG. 3G has not been processed in Step S1000, the step is returned to Step S600.

In Step S600, the differential spectrum is calculated by deducting one or two or more of the small spectrum group of FIG. 3B specified as the fluorescence spectrum of FITC, the differential spectrum (H) specified as the fluorescence spectrum of PE, and the differential spectrum (I) determined as the fluorescence spectrum of PE-TR from the small spectrum group of FIG. 3G. The differential spectrum (J) that is obtained by deducting the small spectrum group of FIG. 3B from the small spectrum group of FIG. 3G matches the fluorescence wavelength distribution pattern of PE-Cy5 if the reference data is referenced (refer to FIG. 7). Therefore, in Step S800, the differential spectrum (J) is determined as the fluorescence spectrum of PE-Cy5 and is stored. Since the differential spectra of all of the fluorescent pigments are determined in Step S900, Step S60 is ended, and the step proceeds to Step S70.

By the above processing, the differential spectrum J is specified with the small spectrum group of FIG. 3B as the fluorescence spectrum of FITC, the differential spectrum (H) as the fluorescence spectrum of PE, the differential spectrum (I) as the fluorescence spectrum of PE-TR, and the differential spectrum (J) as the fluorescence spectrum of PE-Cy5.

In the fluorescence correction operation (Step S70) that follows, the fluorescence intensity is calculated, with regard to each fluorescent pigment of FITC, PE, PE-TR, and PE-Cy5, using the fluorescence wavelength distribution of each of the small spectrum group of FIG. 3B and the differential spectra (H), (I), and (J). Specifically, the detection value from each light detector is corrected, with regard to each fluorescent pigment of FITC, PE, PE-TR, and PE-Cy5, using the inverse matrix of a lean-in matrix in which the fluorescence wavelength distribution of each of the small spectrum group of FIG. 3B and the differential spectra (H), (I), and (J) is arranged as a column vector.

3. Fluorescence Intensity Calculation Device and Fluorescence Intensity Calculation Program The fluorescence intensity calculation device and the fluorescence intensity calculation program according to embodiments include the sections for executing each procedure of the fluorescence intensity correction method described above, and include the steps that execute each procedure. FIG. 8 is a block diagram illustrating the functional configuration of the fluorescence intensity calculation device 1 according to an embodiment. The fluorescence intensity calculation device 1 includes a flow cytometer 10, a CPU 20, a memory 30, a hard disk 40, and a user interface.

Input sections such as a mouse 51 and a keyboard 52 that receive inputs of the fluorescent pigment information by the user (refer to Step S10) are included in the user interface. The fluorescence intensity calculation program and reference data 42 of each fluorescent pigment are stored and stored in the hard disk 40 that is a storing section.

The flow cytometer 10 performs measurement of microparticles (samples) on which fluorescent pigments are labeled (refer to Step S30). The flow cytometer 10 receives, by irradiating light on microparticles that are multiply labeled by a plurality of fluorescent pigments, the fluorescence emitted from excited fluorescent pigments by a plurality of light detectors having different light-receiving wavelength bands. Further, detection values are collected from each light detector and the fluorescence spectra of each fluorescent pigment are obtained as one spectrum group. Furthermore, the flow cytometer 10 also detects scattered light emitted from the microparticles.

Information relating to the obtained spectrum group is displayed on a user interface (display 61) under the control of an operation system (OS) 43. The spectrogram of the spectrum group displayed on the display 61 may be used by the user for designating the component group of the spectrum group using the mouse 51 or the keyboard 52 (refer to Step S50). Further, a two-dimensional correlation diagram including the scattered light information of the microparticles is also displayed on the display 61 and is used for designating the microparticle group of which the user performs analysis (refer to Step S40).

In addition, information relating to the spectrum group is processed by the fluorescence intensity calculation program started under the control of the operating system (OS) 41, and the steps corresponding to each procedure after Step S50 described above are executed.

The fluorescence intensity calculation program is able to be recorded on a computer-readable recording medium. Although the recording medium is not particularly limited as long as it is a computer-readable recording medium, specifically, for example, a disc-shaped recording medium such as a floppy disk or a CD-ROM is used. Further, a tape-type recording medium such as a magnetic tape may be used.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A fluorescence intensity correction method comprising:
receiving, by a plurality of light detectors having different light-receiving wavelength bands, fluorescence emitted from fluorescent pigments that are excited by irradiating light on microparticles that are multiply labeled by a plurality of fluorescent pigments, collecting detected values from each light detector, and obtaining a fluorescence spectrum of each fluorescent pigment as one spectrum group;
separating the obtained spectrum group into a plurality of small spectrum groups;
comparing the separated small spectrum groups with a fluorescence wavelength distribution of each fluorescent pigment, which is obtained in advance, and specifying the small spectrum groups as the fluorescence spectrum of a fluorescent pigment of the plurality of fluorescent pigments;
comparing a differential spectrum between small spectrum groups that are not specified as the fluorescence spectrum of any fluorescent pigment and one or more specified small spectrum groups with the fluorescence wavelength distribution of unspecified fluorescent pigments, which are obtained in advance, and specifying the differential spectrum as the fluorescence spectrum of a fluorescent pigment of the plurality of fluorescent pigments; and
calculating the intensity of fluorescence emitted from each fluorescent pigment using a fluorescence wavelength distribution of the small spectrum group or the differential spectrum with regard to fluorescent pigments in which the small spectrum group or the differential spectrum is specified and using the fluorescence wavelength distribution, which is obtained in advance, with regard to fluorescent pigments in which the small spectrum group or the differential spectrum is not specified.

2. The fluorescence intensity correction method according to claim 1, wherein the intensity of the fluorescence emitted from each fluorescent pigment is calculated by arranging the fluorescence wavelength distribution of the small spectrum group or the spectrum differential as a column vector with regard to fluorescent pigments in which the small spectrum group or the differential spectrum is specified and using an inverse matrix of a leak-in matrix that is the fluorescence wavelength distribution obtained in advance arranged as a column vector with regard to fluorescent pigments in which the small spectrum group or the differential spectrum is not specified.

3. The fluorescence intensity correction method according to claim 2, wherein the spectrum group is separated into a plurality of small spectrum groups by independent component analysis or principal component analysis.

4. A fluorescence intensity calculation method comprising:
receiving, by a plurality of light detectors having different light-receiving wavelength bands, fluorescence emitted from fluorescent pigments that are excited by irradiating light on microparticles that are multiply labeled by a plurality of fluorescent pigments, collecting detected values from each light detector, and obtaining a fluorescence spectrum of each fluorescent pigment as one spectrum group;
separating the obtained spectrum group into a plurality of small spectrum groups;
comparing the separated small spectrum groups with a fluorescence wavelength distribution of each fluorescent pigment, which is obtained in advance, and specifying the small spectrum groups as the fluorescence spectrum of a fluorescent pigment of the plurality of fluorescent pigments;
comparing a differential spectrum between small spectrum groups that are not specified as the fluorescence spectrum of any fluorescent pigment and one or more specified small spectrum groups with the fluorescence wavelength distribution of unspecified fluorescent pigments, which are obtained in advance, and specifying the differential spectrum as the fluorescence spectrum of a fluorescent pigment of the plurality of fluorescent pigments; and calculating the intensity of fluorescence emitted from each fluorescent pigment using a fluorescence wavelength distribution of the small spectrum group or the differential spectrum with regard to fluorescent pigments in which the small spectrum group or the differential spectrum is specified and using the fluorescence wavelength distribution, which is obtained in advance, with regard to fluorescent pigments in which the small spectrum group or the differential spectrum is not specified.

5. A fluorescence intensity calculation device comprising:

a measuring section that receives, by a plurality of light detectors having different wavelength bands, fluorescence emitted from fluorescent pigments that are excited by irradiating light on microparticles that are multiply labeled by a plurality of fluorescent pigments, collects detected values from each light detector, and obtains a fluorescence spectrum of each fluorescent pigment as one spectrum group; and a calculating section that calculates the intensity of fluorescence emitted from each fluorescent pigment by separating the obtained spectrum group into a plurality of small spectrum groups, comparing the separated small spectrum groups with a stored fluorescence wavelength distribution of each fluorescent pigment, which is obtained in advance, and specifying the small spectrum groups as the fluorescence spectrum of a fluorescent pigment of the plurality of fluorescent pigments, and comparing a differential spectrum between small spectrum groups that are not specified as the fluorescence spectrum of any fluorescent pigment and one or more specified small spectrum groups with the stored fluorescence wavelength distribution of unspecified fluorescent pigments, and specifying the differential spectrum as the fluorescence spectrum of a fluorescent pigment of the plurality of fluorescent pigments, using a fluorescence wavelength distribution of the small spectrum group or the spectrum differential with regard to fluorescent pigments in which the small spectrum group or the differential spectrum is specified and using the stored fluorescence wavelength distribution with regard to fluorescent pigments in which the small spectrum group or the differential spectrum is not specified.

6. The fluorescence intensity calculation device according to claim 5, further comprising:

an inputting section that receives input of information relating to fluorescent pigments used in fluorescent labeling of microparticles; and a storing section that stores the fluorescence wavelength distribution of each fluorescent pigment obtained in advance.

7. A computer readable medium storing a fluorescence intensity correction program, which when executed, is configured to cause an apparatus to:

receive, by a plurality of light detectors having different wavelength bands, fluorescence emitted from fluorescent pigments that are excited by irradiating light on microparticles that are multiply labeled by a plurality of fluorescent pigments, collect detected values from each light detector, obtain a fluorescence spectrum of each fluorescent pigment as one spectrum group, and separate the spectrum group into a plurality of small spectrum groups;

compare the separated small spectrum groups with a stored fluorescence wavelength distribution of each fluorescent pigment and specify the small spectrum groups as the fluorescence spectrum of a fluorescent pigment of the plurality of fluorescent pigments;

compare a differential spectrum between small spectrum groups that are not specified as the fluorescence spectrum of any fluorescent pigment and one or more specified small spectrum groups with the stored fluorescence wavelength distribution of unspecified fluorescent pigments, and specify the differential spectrum as the fluorescence spectrum of a fluorescent pigment of the plurality of fluorescent pigments; and calculate the intensity of fluorescence emitted from each fluorescent pigment using a fluorescence wavelength distribution of the small spectrum group or the differential spectrum with regard to fluorescent pigments in which the small spectrum group or the differential spectrum is specified and using the stored fluorescence wavelength distribution with regard to fluorescent pigments in which the small spectrum group or the differential spectrum is not specified.

* * * * *